United States Patent [19]

Murayama

[11] Patent Number: 5,046,077
[45] Date of Patent: Sep. 3, 1991

[54] CONTINUOUS LATTICE CONSTANT MEASURMENTS AND APPARATUS THEREFOR WITHIN A HEAT FURNACE

[75] Inventor: Hiromu Murayama, Tokyo, Japan

[73] Assignee: U.S. Philips Corporation, New York, N.Y.

[21] Appl. No.: 539,091

[22] Filed: Jun. 15, 1990

[30] Foreign Application Priority Data

Jun. 16, 1989 [JP] Japan .................................. 1-152208

[51] Int. Cl.⁵ .................... G01N 23/20; G01N 23/207
[52] U.S. Cl. ........................................ 378/80; 378/73; 378/81
[58] Field of Search ............................. 378/73, 80, 81

[56] References Cited

U.S. PATENT DOCUMENTS

| | | | |
|---|---|---|---|
| 3,113,209 | 12/1963 | Shimula | 378/73 |
| 3,816,747 | 6/1974 | Kishino | 378/73 |
| 4,301,364 | 11/1981 | Goebel | 378/73 |
| 4,364,122 | 12/1982 | Wölfel et al. | 378/73 |
| 4,634,490 | 1/1987 | Tatsumi et al. | 378/73 |
| 4,961,210 | 10/1990 | Fatemi | 378/73 |

Primary Examiner—Edward P. Westin
Assistant Examiner—Kim-Kwok Chu
Attorney, Agent, or Firm—Norman N. Spain

[57] ABSTRACT

The invention discloses a method and an apparatus for measuring lattice spacings in particular of a single crystal during the growth thereof by vapor deposition while located in a heating furnace.

3 Claims, 2 Drawing Sheets

CONTINUOUS LATTICE CONSTANT MEASURMENTS AND APPARATUS THEREFOR WITHIN A HEAT FURNACE

BACKGROUND OF THE INVENTION

The present invention relates to a method of and apparatus for measuring the lattice constant ratio of a crystal, in particular, a single crystal during growth using X-ray diffraction.

DESCRIPTION OF THE RELATED ARTS

An ideal mixed crystal (solid solution, for example, $Ga_{1-x}Al_xAs$) has a linear relation between a lattice constant and a chemical composition). The transformation of a crystal caused by the injection, diffusion and epitaxy of ions generally affects the lattice constant, and therefore, by measuring the change of the lattice constant, it can be determined whether or not the crystal has reached a required composition. This measurement can be carried out by using X-ray diffraction. When X-ray parallel beams of a wavelength λ enter a crystal, the lattice spacing of which is d, at an angle $\theta$, diffraction occurs when the following Bragg condition is satisfied.

$$2d \sin \theta = n\lambda$$

The variation $\Delta d/d$ observed when an X-ray beam is diffracted at an angle of $2\theta$ is determined by the extension ($\Delta\theta$) of the incident angle and the extension ($\Delta\lambda/\lambda$) of the wavelength of the beam.

A conventional lattice constant ratio measuring apparatus for performing such measurement is shown in FIG. 3 of the drawing. In this figure, numeral 1 denotes an X-ray tube; 2 denotes a specimen radiated with an X ray from this X-ray tube which is converted to a monochrome via a quarternary crystal monochrometer 3, for example, a crystal of indium gallium arsenic phosphorous (InGaAsP) which is vapor-epixitially grown on a substrate. Numeral 4 denotes a specimen stand which also serves as a heating mechanism for this specimen 2. Numeral 5 denotes a detector (counter tube) for detecting an X-ray diffraction image from the above-mentioned specimen 2. In this kind of measuring apparatus, the specimen stand 4 is made to turn in one plane, for example, in a plane parallel to the paper plane, and a plane perpendicular to this plane in FIG. 3, by a proper turning mechanism (not shown) so that an X-ray diffraction image from the specimen 2 is positioned so as to be correctly detected by the detector 5. After the specimen stand 4 is fixed to this position, the specimen mount 4 is turned (scanned) in a range of angles of substantially 2° within a plane which includes the X-ray tube 1, the quarternary crystal monochrometer 3, and the detector 5 and a locking curb is measured. The deviation (mismatch) in the crystal orientation of indium phosphorous (InP) and indium gallium phosphorous (InGaAsP) from the half-value width center of this locking curb is automatically calculated so that the physical properties of a specimen are evaluated.

In the above-mentioned conventional measuring apparatus, however, the specimen 2 is taken out of the heating furnace. Therefore, a fine change in the crystal orientation of a specimen in which a crystal is being grown in a heating furnace cannot be measured continuously, for example, in units of minutes.

In order to achieve this object, the above-mentioned conventional apparatus should be built into a heating furnace. However, the inside of such heating furnace is generally at high temperature of 600° C. or thereabouts and the turning mechanism of the specimen stand 4 cannot be maintained with high precision.

SUMMARY OF THE INVENTION

An object of this invention is to provide a new an improved method and apparatus of measuring the crystal constant ratio of a crystal substrate being grown.

According to one aspect of the invention in measuring the lattice constant ratio present, in the outside of a heating furnace, a goniometer, positioned in the outside of a heating furnace, on said substrate white said substrate is a heating furnace is turned about the crystal substrate disposed inside the above-mentioned heating furnace and the rotation of the goniometer is stopped at the position at which X-ray diffraction radiated to the above-mentioned substrate from an X-ray tube is detected by a detector so as to prescribe the crystal orientation of the above-mentioned substrate and the position of the above-mentioned X-ray tube. Next, while a crystal different from the above-mentioned substrate crystal is grown on the above-mentioned substrate, the ratio lattice constant of the above-mentioned substrate is measured against that of the above-mentioned different crystal.

According to a further aspect of the invention X-ray diffraction apparatus for measuring the lattice constant ratio of the present invention comprises a heating furnace, a movement base positioned outside the heating furnace, a mechanism for turning the movement base in an arbitrary direction about a specimen substrate positioned in the above-mentioned heating furnace, a mechanism for fixing the movement base, an X-ray tube for radiating the above-mentioned specimen with X rays from outside of the heating furnace, a detector for detecting X rays reflected by the specimen, and a goniometer provided on the movement base.

Figure 1:
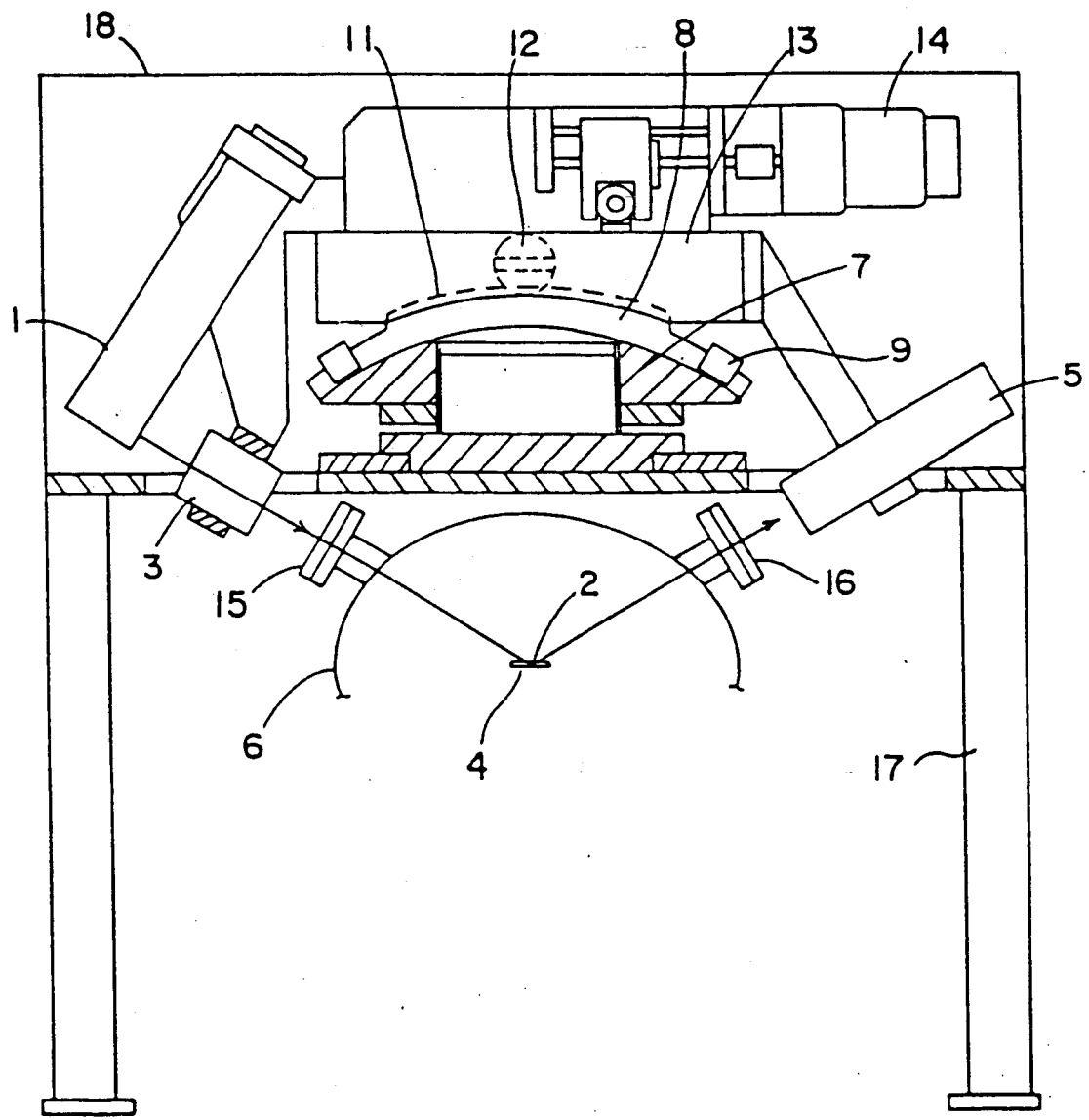
FIG. 1 is a cross-sectional view of the apparatus for measuring the lattice constant ratio of a specimen.

In the method of and apparatus for measuring the lattice constant ratio of a specimen of the present invention, the lattice constant ratio of a specimen during heating in a heating furnace is continuously measured.

An embodiment of the method of and apparatus for measuring the lattice constant ratio of a specimen of the present invention will be explained with reference to FIG. 1 and FIG. 2 of the drawing.

Figure 2:
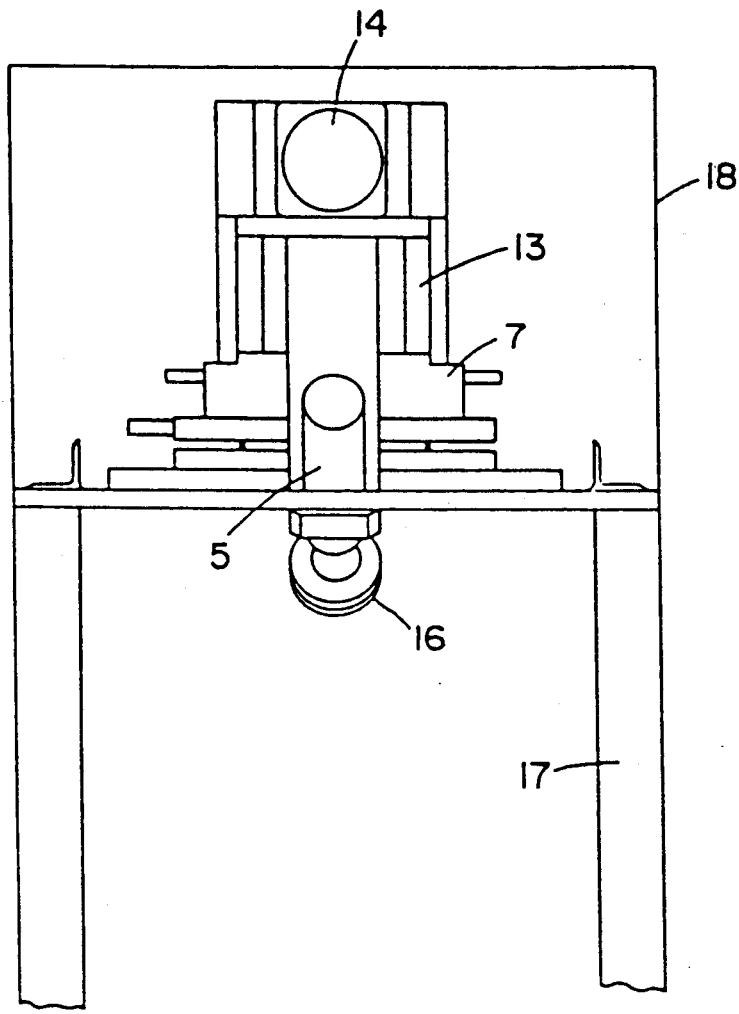
FIG. 2 is a side view of the apparatus for measuring the lattice constant ratio of a specimen.
Figure 3:
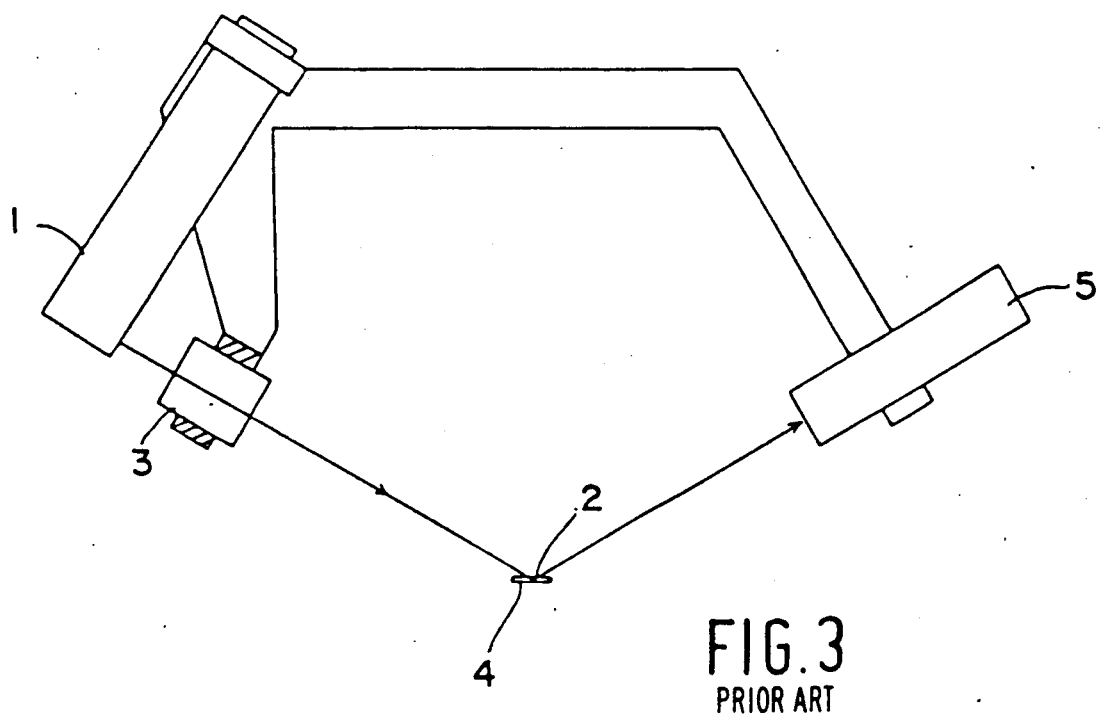
FIG. 3 is a view to explain the conventional apparatus for measuring the lattice constant ratio of a specimen.

As shown in FIGS. 1 and 2, in the present invention, a gyroscope mechanism consisting of a rotatable movement base 8, a movement block 13, and a gyro fixation section 7 are positioned outside a heating furnace 6 in one plane about the specimen 2 positioned on specimen mound positioned inside the heating furnace 6; for example, in a plane parallel to the paper plane and a plane perpendicular to this plane in FIG. 1. Six fixation mechanisms 9, using, for example, a magnet are mounted to the movement base 8 of the gyroscope mechanism. The movement base 8 is supported rotatably by the spherical shaped sheet of the gyro fixation section 7 fixed to the heating furnace 6. By fixing the fixation mechanisms 9 to the gyro fixation section 7, it is possible to fix the movement base 8 at any angle and position with respect to the specimen 2. A worm gear 11, along an arch-like surface about the specimen 2, is provided on the top surface of the movement base 8 and a worm 12 is made to engage the worm gear 11.

In addition, the X-ray tube 1, the quarternary crystal monochrometer 3 and the detector 5 are positioned outside the heating furnace 6 so as to be in a predetermined position relative to each other. These are mounted on a movement block 13 provided likewise outside the heating furnace 6. The worm 12 that engages with the worm gear 11 is rotatably supported by the movement block 13. As a result, when the worm 12 is turned by a motor 14, the movement block 13 is turned in a range of, for example, 2° in a plane parallel to a plane which includes the X-ray tube 1, the quarternary crystal monochrometer 3 and the detector 5.

Further denote X-ray transmission windows 15 and 16 are provided the outer wall of the heating furnace 6; a goniometer supporting rack 17 for supporting the goniometer; and an X-ray shield cover 8 is also provided.

The goniometer is a mechanism for prescribing the angle between the specimen mount 4 and the detector (counter tube) which is disposed on the gyroscope mechanism.

The method for measuring the lattice constant of a crystal specimen according to the the present invention employing the apparatus of the invention is as follows. Movement block 13 in which the X-ray tube 1, the four-crystal monochrometer 3 and the detector 5 are mounted is turned in an arbitrary direction about the specimen 2 inside the heating furnace 6 via the above-mentioned gyroscope mechanism, and X-rays from the X-ray tube 1 are radiated to the specimen 2 inside the heating furnace 6 via the quarternary crystal monochrometer 3 and the X-ray transmissive window 1 causing the fixation mechanisms 9 to be activated at the position at which its X-ray diffraction image is detected by the detector 5 via the X-ray transmissive window 16 so that the movement block 13 is fixed to the gyro fixation section 7. Then, turning the movement block 13 along the worm gear 11 of the movement base 8 via the worm 12 driving the motor 14 in a plane parallel to the plane which includes the X-ray tube 1, the four-crystal monochrometer 3 and the detector 5, enables the lattice constant ratio of a specimen in a heated state inside the heating furnace 6 to be measured, for example, in units of minutes.

As regards the gyroscope mechanism to be used, a conventional mechansim is known whereby a shaft that rotates in one plane is connected to a shaft that rotates in a plane perpendicular to the above-mentioned plane.

As has been described above, according to the method of and apparatus for measuring the lattice constant ratio of a specimen, it has great advantages in that the lattice constant ratio of specimen during crystal growth can be measured easily and chronologically.

I claim:

1. A method of measuring lattice constant ratios of crystals comprising the steps of:
    turning a goniometer on the outside of a heating furnace in an arbitrary direction about a crystal substrate disposed inside said heating furnace;
    radiating said substrate with X-radiation from an X-ray tube;
    stopping the rotation of said goniometer at the position at which X-ray diffraction radiated on said substrate from an X-ray tube is detected by a detector;
    prescribing the crystal orientation of said substrate and the position of said X-ray tube;
    growing a crystal different from said substrate crystal on said substrate; and
    measuring the ratio of the lattice constant of said different crystal to that of said substrate while said crystal different from said substrate crystal is being grown on said substrate.

2. An X-ray diffraction apparatus for measuring lattice constant ratios of crystals, comprising:
    a heating furnace;
    a movement base positioned on the outside of said heating furnace;
    a mechanism for turning the movement base positioned outside of said heating furnace in an arbitrary direction about a specimen crystal substrate disposed in said heating furnace;
    a mechanism for fixing said movement base;
    an X-ray tube for radiating the said specimen with X-ray from outside of said heating furnace;
    a detector for detecting X-rays reflected by said specimen crystal substrate; and
    a goniometer provided on said movement base.

3. An X-ray diffraction apparatus for measuring lattice constant ratios of crystals, comprising:
    a heating furnace;
    a movement base positioned on the outside of said heating furnace;
    a gyroscope mechanism for turning the movement base, positioned outside of said heating furnace, in an arbitrary direction about a specimen crystal substrate disposed in said heating furnace;
    a mechanism for fixing said movement base;
    an X-ray tube for radiating the said specimen with X-ray from outside of said heating furnace;
    a detector for detecting X-rays reflected by said specimen crystal substrate; and
    a goniometer provided on said movement base.

* * * * *